United States Patent [19]
McKinney

[11] 4,279,824
[45] Jul. 21, 1981

[54] METHOD AND APPARATUS FOR PROCESSING HERBACEOUS PLANT MATERIALS INCLUDING THE PLANT CANNABIS

[76] Inventor: Laurence O. McKinney, 881 Massachusetts Ave., Cambridge, Mass. 02139

[21] Appl. No.: 90,375

[22] Filed: Nov. 1, 1979

[51] Int. Cl.$^3$ ............................................. C07D 311/78
[52] U.S. Cl. ................................ 260/345.3; 568/743; 422/164
[58] Field of Search ....................... 260/345.3; 568/743

[56] References Cited

PUBLICATIONS

Mechoulam et al., Tetrahedron Letters, pp. 2339–2341 (1969).
Levine, JACS, 66, 1868 (1944).

*Primary Examiner*—Nicky Chan
*Attorney, Agent, or Firm*—David A. Jackson

[57] ABSTRACT

Herbaceous plant material is processed by heating it to within a specific temperature range for a predetermined period of time, within a novel processing apparatus. The plant material is held in an atmosphere whose oxygen content is controlled to convert a chemical found in the material into a more useful form without significant degradation taking place during the conversion process. In the instance wherein the herbaceous material is the plant substance cannabis, the material is heated in an inert atmosphere in accordance with the inventive method to carry out a step of decarboxylation which changes cannabinolic acid present in cannabis into the psychoactive drug or chemical delta-9 Tetrahydrocannabinol. Control of decarboxylation in accordance with the invention prevents destructive pyrolysis and degradative oxidation of the delta-9 tetrahydrocannabinol. Oxidative degradation is further prevented by storing the processed material in an inert atmosphere, while controlled degradation may be achieved by selective oxidative heating.

10 Claims, 3 Drawing Figures

METHOD AND APPARATUS FOR PROCESSING HERBACEOUS PLANT MATERIALS INCLUDING THE PLANT CANNABIS

BACKGROUND OF THE INVENTION

The instant invention is concerned with the field of herbaceous plant materials from which there may be realized in one form or another medicinal compounds such as drugs and other pharmaceuticals.

At the present time, the herbaceous plant material cannabis is grown, processed, and utilized in the United States under Government regulations and controlled by Government agencies. Research and study is carried out under the control of Federal Agencies, and work is being carried out in the medical field by medical laboratories and others relative to the use of the drug as a therapeutic pharmaceutical, and relative to its use also as a social euphoriant.

It is understood that difficulties are often encountered by those engaged in government research and medical studies dealing with cannabis. The government has for some time provided researchers with plant material both in loose form and in pre-rolled cigarettes. Despite careful controls on the varieties grown under government supervision to provide this experimental material, the amount of delta-9 tetrahydrocannabinol can still vary widely from sample to sample. The only current methods in use that provide a means to decarboxylate the cannabinolic acid in the plant to the active delta-9 tetrahydrocannabinol are destructive both to the plant material, and to whatever delta-9 tetrahydrocannabinol is actually created.

Cannabis is known to contain the chemicals delta-9 tetrahydrocannabinol and cannabidiol, 95% of which in nature are present in the precursor acid states. This suggests that these acids are the original products of biosynthesis, and that the non-acid forms are decarboxylation products according to the following reactions:

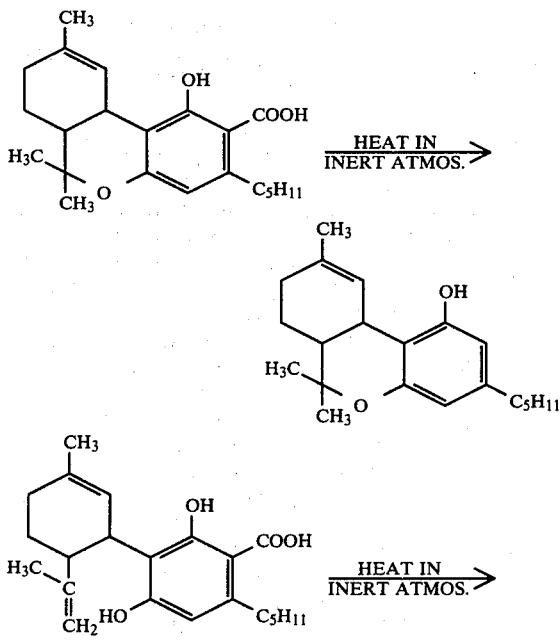

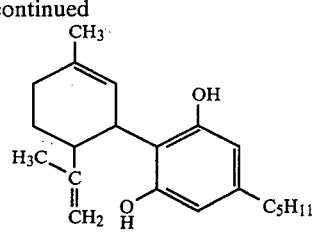

Both delta-9 tetrahydrocannabinol and cannabidiol exhibit no pyschoactive properties in their acid forms. Before any psychoactive activities are affected, delta-9 tetrahydrocannabinol and cannabidiol must be decarboxylated. This is generally accomplished by the administration of heat to the point at which the carboxylic acid radical is removed from the molecule.

It is theorized that delta-9 tetrahydrocannabinol serves the plant as a chemical deterrent both to birds, and to insects. Those birds which would eat the oil-rich hempseed are repelled by minute amounts of delta-9 tetrahydrocannabinol, which is especially present in the flowering tops of the plant. Later, when the seed is mature and hard, the coverings or bracts part, exposing the seed. It can then be eaten by the birds, which void a percentage of the hard seeds which make the passage through the bird's digestive tract intact. In this way the plant is propagated, since insect pollination is rendered impossible by the repellent nature of the delta-9 tetrahydrocannabinol. As in the case of many active and effervescent substances, delta-9 tetrahydrocannabinol is easily oxidized upon exposure to the oxygen in the atmosphere, yielding cannabinol, a chemical with no apparent psychoactive or repellant properties. (J. Levine, J. American Chem. Soc. 66, 1868 (1944). The oxidation reaction is as follows:

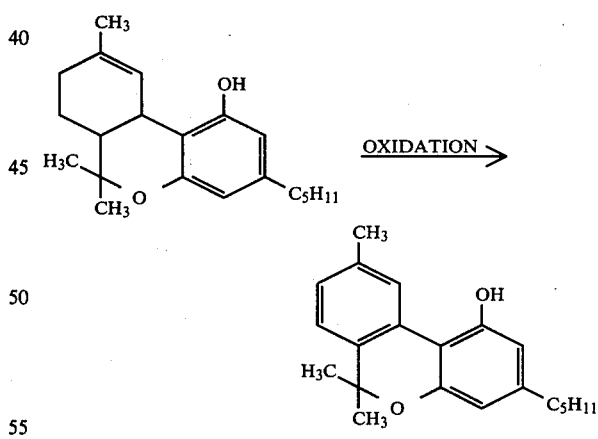

It is suggested that the production of the acid precursor by the plant is to allow a slow and steady production of delta-9 tetrahydrocannabinol by means of the heat of the sun during the growing season of the plant. In this way, as delta-9 tetrahydrocannabinol oxidizes to cannabinol, it is constantly being replaced by fresh supplies realized by the decarboxylation of the less active acid form. It has been found that, upon harvest, nearly 95% of the possible delta-9 tetrahydrocannabinol is still in the acidic, non-active form.

An effective method and associated apparatus are therefore needed to accomplish the rapid and efficient conversion of the plant substance to maximize the content of the active ingredient.

SUMMARY OF THE INVENTION

The present invention relates to an improved method and associated apparatus for processing herbaceous plant substances such as the plant cannabis, including the varieties *Cannabis sativa, Cannabis indica, Cannabis ruderalis,* and others by heating the plant material in an atmosphere of controlled oxygen content to a temperature of up to about 120° C., for a period of time sufficient to promote the decarboxylation of cannabinolic to the useful form of delta-9 tetrahydrocannabinol. In one embodiment, the process may be conducted in an inert environment, and the heating step may proceed for a period of up to approximately one hour.

The method of the present invention further contemplates the extraction of the active chemical delta-9 tetrahydrocannabinol from the plant substance to facilitate the application of the purified extract for medical and pharmaceutical use. In this instance, the inert environment may comprise a liquid solvent within which the plant material may be immersed and thereafter heated, whereby maximum decarboxylation may be achieved without the concurrent oxidation of the desired end product in the process of leaching the end product from the plant material.

The end product which may be obtained pursuant to the present process, delta-9 tetrahydrocannabinol, is useful in the treatment of glaucoma, the harmful side effects of chemotherapy utilized in the treatment of cancer, hypertension and other illnesses where an analgesic or smooth muscle relaxant is required.

The present invention includes an apparatus for use in the practice of the present method which comprises a container having thermostatically controlled heating means disposed therein, and fluid-pervious container means disposed within the apparatus to retain said plant material therein. In one embodiment of the invention, the inert medium may comprise water.

Accordingly, it is a principal object of the present invention to provide a method and apparatus for processing herbaceous plant material under controlled conditions to maximize the conversion of a chemical found within the plant material to a more useful form.

It is a further object of the present invention to provide a method as aforesaid wherein the plant material comprises the plant cannabis and the more useful form of the chemical comprises delta-9 tetrahydrocannabinol.

A yet further object of the present invention is to provide a method as aforesaid wherein the plant cannabis is subjected to a controlled decarboxylation to convert cannabinolic acid to delta-9 tetrahydrocannabinol without oxidation of the resulting product.

It is a yet further object of the present invention to provide a method as aforesaid wherein reaction time, oxidative degradation and pyrolytic destruction of the end product are minimized.

It is a yet further object of the present invention to provide an apparatus for the practice of the method of the present invention which is of simple and inexpensive construction and provides a temperature and environment controlled receptacle for the herbaceous plant material.

Other objects and advantages will become apparent from a consideration of the ensuing specification which proceeds with reference to the following drawings.

DETAILED DESCRIPTION

Figure 1:
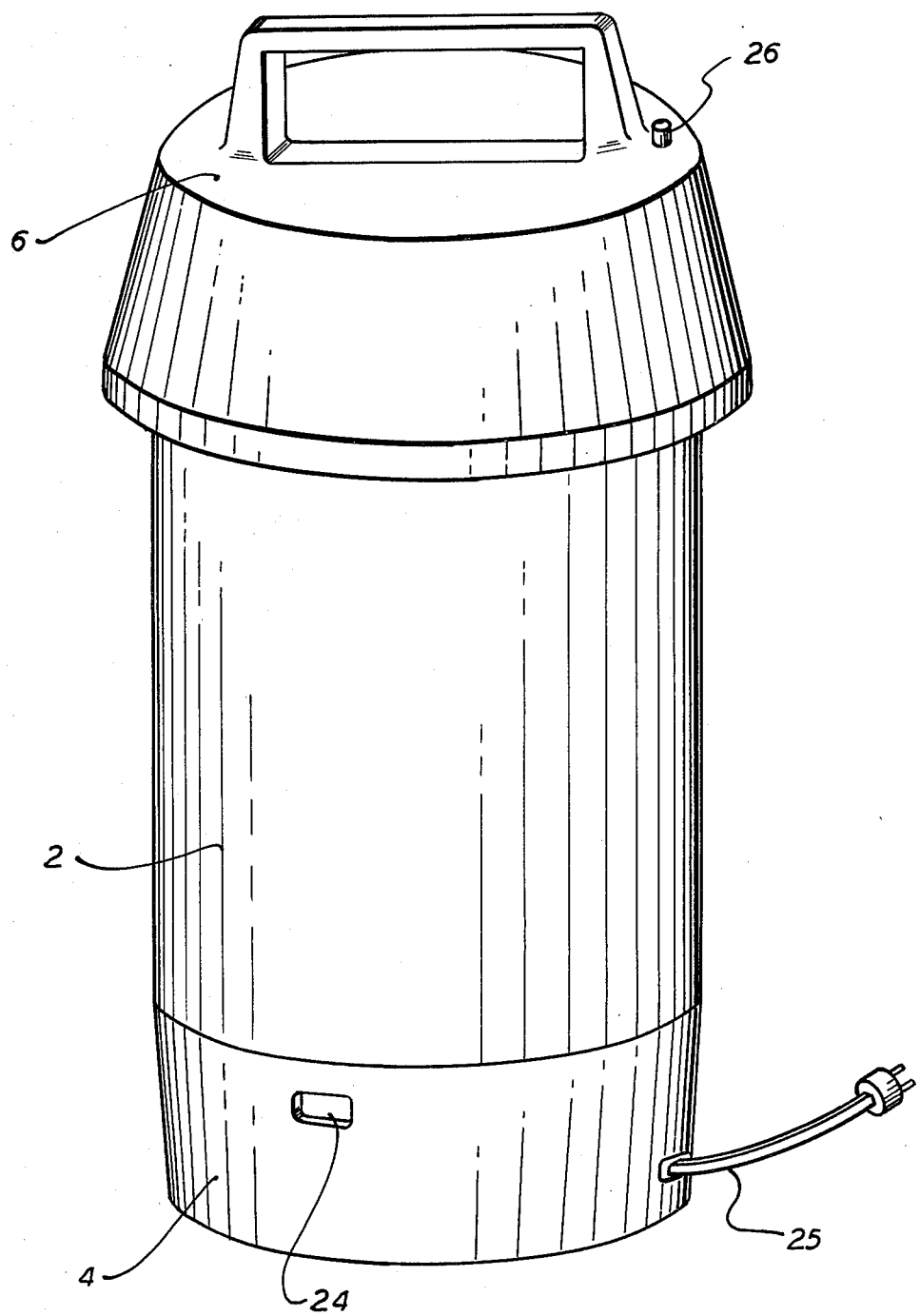
FIG. 1 is a perspective view of one desirable form of heating apparatus of the invention.

The apparatus shown in the drawings has been specially designed to provide means for processing a herbaceous plant material such as cannabis. The apparatus may, however, be used in processing other substances in connection with which it may be desired to produce a chemically changed compound by the use of controlled heating as well as in cases where the chemically changed material is thereafter required to be further processed or maintained in a state such that no further change occurs.

The apparatus is hereinafter described in detail in connection with the processing of cannabis to produce the psychoactive substance delta-9 tetrahydrocannabinol, however, it should be understood that the apparatus shown in the drawings may be utilized for various other applications and the specific procedures herein disclosed may be varied to deal with other thermally reactive materials.

The design of the apparatus shown in the drawings is based on a recognition of certain limiting factors. In order to change cannabinolic acid present in cannabis into delta-9 tetrahydrocannabinol, and at the same time minimize the subsequent oxidation of the unstable delta-9 tetrahydrocannabinol into cannabinol, it is necessary to limit or eliminate the presence of atmospheric oxygen during the decarboxylation process.

Further, in heating the cannabis, whether in a gaseous or liquid medium, it is necessary to use temperatures which, although sufficiently high to carry out the desired chemical change involved in decarboxylation, will not be of such intensity as to destroy the decarboxylated product. This objective may be realized, by properly controlling the manner in which the cannabis is heated. The cannabis may accordingly be subjected to heating for approximately one hour during which the heating temperatures are held in a range of not lower than 95° C. and no higher than 120° C.

Figure 2:
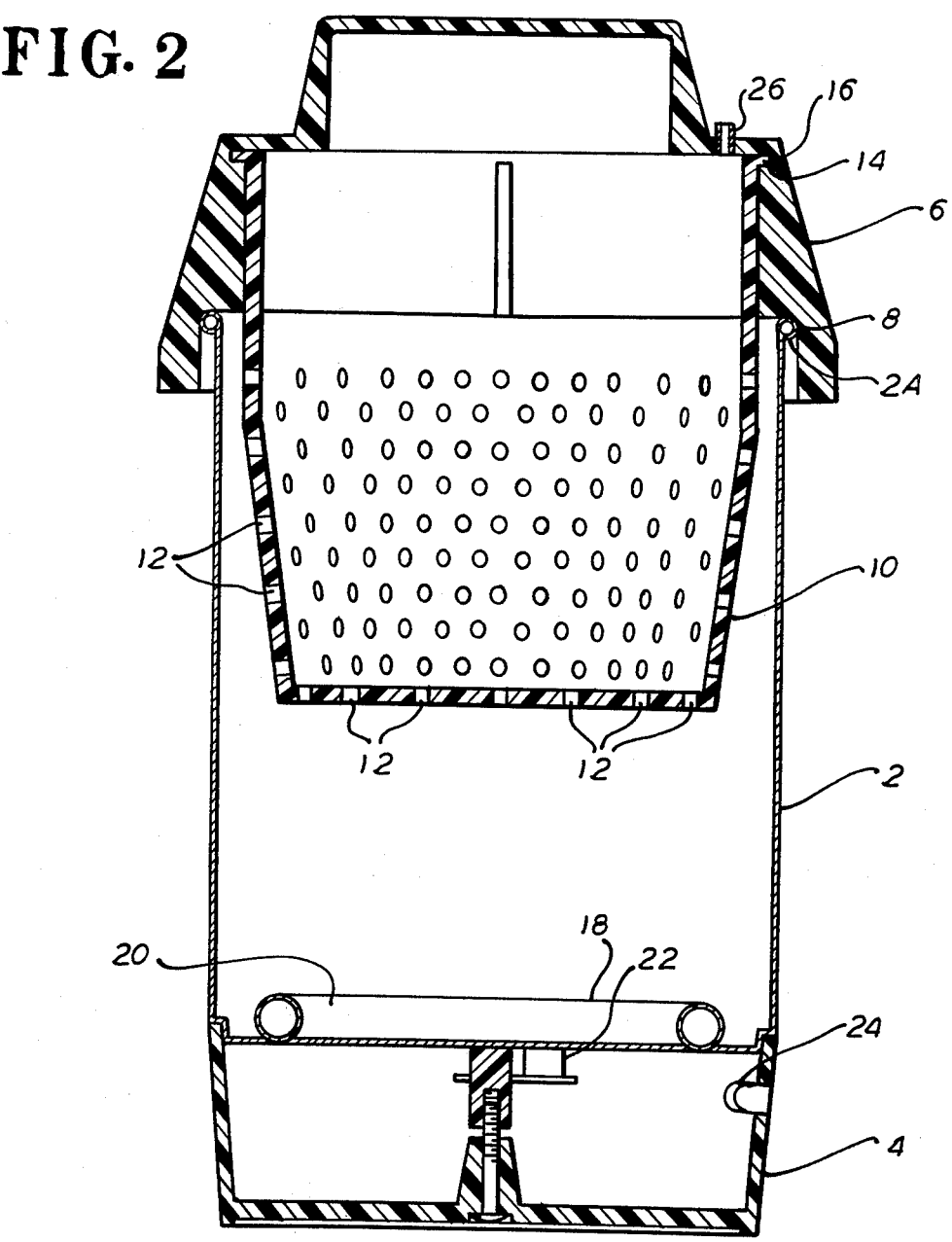
FIG. 2 is a vertical cross section view taken centrally of the structure shown in FIG. 1.
Figure 3:
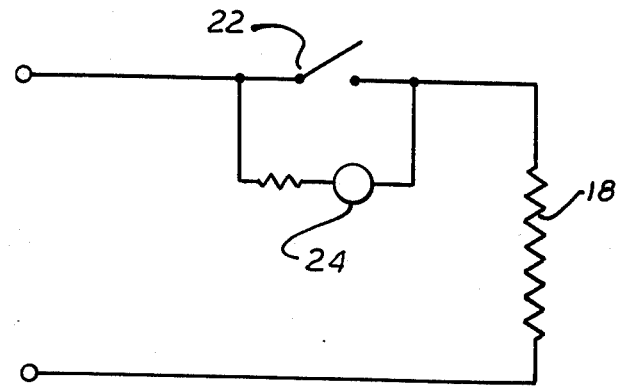
FIG. 3 is a schematic diagram illustrating the assembly and operation of the heating means of the apparatus of FIG. 1.

Referring more in detail to the heating apparatus illustrated in FIGS. 1 to 3 inclusive, numeral 2 denotes a container body which is suitable for carrying out decarboxylation of small quantities of cannabis such as may be required in preparing laboratory samples and the like. The container member 2 may be metal, plastic, glass or other suitable material and is preferably constructed of a cylindrical shape as shown. The container 2 is closed at its lower portion by a base 4, and is open at its upper end to provide for materials such as cannabis stalks being placed therein. A cover 6 is arranged to be fitted over a relieved upper edge 2A of the container in a position to be sealed by a sealing or packing element 8. The sealing element, for example, may be an O-ring disposed within the perimeter of cover 6 or a bead-like lip as shown. Naturally, cover 6 may be designed to be sealably engagable with container 2 in a variety of ways all falling within the scope of the present invention, and the invention is therefore not limited to the specific embodiments illustrated and described above.

Referring now to FIG. 2, cover 6 is shown in snap-fittable engagement with a secondary container or basket 10 which is provided with a plurality of openings 12 to permit the unobstructed movement of the heated medium therethrough. Referring to FIG. 2, a quantity of plant material, not shown, is located within basket 10 and is thereafter suspended from cover 6 by snap-fittable engagement of circumferential rim 14 of the basket with corresponding recess 16 disposed as indicated within cover 6. Again, though the foregoing means of releasably engaging cover 6 and basket 10 has been shown, it is to be understood that alternate engagement means may be employed, such as regularly spaced projections radiating inwardly from the inner surface of cover 6 to mate with corresponding detents disposed in the outer upper surface of basket 10. The foregoing is therefore merely illustrative of such engagement means, and the invention is therefore not limited to the specific construction illustrated herein.

Referring particularly to FIG. 2, a fluid medium, such as ordinary tap water, may then be placed inside container 2 to a level wherein it will reside just below the bottom of basket 10. A heating means 18 is provided at the bottom of container 2 at its interface with base 4. Heating means 18 as illustrated may comprise a circular heating coil 20 which is provided with electrical connection to a temperature responsive switching means 22 which is disposed in parallel electrical connection with an indicator light 24, as schematically shown in FIG. 3. Switching means 22, which may comprise a thermostatic switch, is constructed to interrupt the supply of electrical current to the heating element 20 when the temperature in the container 2 reaches a level in excess of that proper for the efficient non-destructive heating of the plant material. Heating means 18 may be adapted for alternating current or direct current operation, including battery power, and is connected to the appropriate current supply by power cord 25 shown in FIG. 1.

Referring briefly to FIG. 3, the circuitry of heating means 18 is schematically represented, and it can be seen that thermostatic switching means 22 is located in parallel displacement astride indicator light 24, whereby an increase in the temperature of the environment of container 2 beyond the threshold of the switching means 22 causes switching means 22 to open with the result that heating element 20 is cycled off and indicator light 24 is activated and visibly glows to advise the user that the heating process has been completed. In a particular embodiment, the thermostat may be calibrated for activation at 110° C. so that, in the instance where water is the fluid medium, shut off will not occur until all water has been boiled away.

Referring again to FIGS. 1 and 2, the heating process, in the instance where water is the fluid medium, generates a substantial amount of vapor under pressure which must be vented. Accordingly, the present heating apparatus is provided with a one way air vent 26 which may comprise a check valve, and may, as illustrated, be located in the cover 6. Naturally, location of the check valve is not critical and may be varied in accordance with the skill of the art.

In the operation of the apparatus of the present invention, a quantity of the fluid medium, for example, ordinary tap water, is placed inside container 2. Preferably, the quantity of water is such as to lie below the level occupied by the bottom of basket 10. Further, the quantity of fluid should be such as to assure that heating continues for a period of about one hour. In the present illustration, it has been determined that the employment of a heater coil 20 having an output of 200 watts is capable of raising 6 ounces of water to the boiling point of approximately 100° C. within 10 minutes, and is thereafter capable of totally dissipating the water by boiling and evaporation within 60 minutes. Accordingly, in the instance where water is the medium, up to about 6 ounces are preferably employed, it being understood that the quantity of fluid medium employed can control duration of the heating cycle.

As noted earlier, the method of the present invention is predicated upon the heating of the plant material at a temperature sufficient to cause the rapid decarboxylation of the cannabinolic acid to delta-9 tetrahydrocannabinol, without the conventionally attendant pyrolysis of the end product, and or oxidative degradation. Oxidative degradation is prevented by the employment of the generally inert heating medium, while pyrolysis may be minimized or eliminated while optimum conversion achieved if the heating temperature is maintained within the range of about 95° C. to about 120° C. In a preferred embodiment of the present invention, heating may be conducted at approximately 100° C. for a period of time of approximately one hour. As described above, the apparatus useful in accordance with the present invention is specifically designed to promote heating within the aforementioned parameters and, upon placement of the plant material within basket 10, and the sealable securement of cover 6 in position upon container 2, heating may be commenced by merely connecting the unit to an appropriate electrical outlet.

As noted earlier, it is necessary to limit the intrusion of atmospheric air, while providing an egress for the heated air and moisture realized during the heating procedure. Accordingly, the apparatus as above described provides for sealable exclusion of atmospheric ambient during the heating process, while providing a means for egress of moisture and vapor through vent 26.

As noted above with reference to the plant cannabis, the cannabis may be heated within the temperature range and for the period of time noted, during which decarboxylation occurs and the cannabinolic acid is converted into delta-9 tetrahydrocannabinol. At the end of the heating cycle, heating is discontinued and the decarboxylated material now contains the maximum possible cannabinol content. The thus treated plant material is now ready for use. Storage of the processed plant material for any period of time should be conducted in an inert or oxygen free environment, so as to prevent the degradative oxidation of the active ingredient from taking place.

In a typical instance, a sample of 100 grams of cannabis, including the varieties *Cannabis sativa, Cannabis indica* and *Cannabis ruderalis,* may contain approximately 5 grams of the cannabinolic acid forms, which by the application of the method of the present invention becomes almost completely changed into delta-9 tetrahydrocannabinol, also known as THC. Accordingly, THC may be produced from small quantities of cannabis to a maximum amount obtainable from the particular variety of cannabis processed which, as earlier noted, may vary from one sample and variety of cannabis to the next. For some purposes where the precise determination of THC level is unnecessary, the foregoing technique may be all that is needed to effect complete processing.

Though the foregoing description and accompanying illustrations have dealt with a method and accompanying apparatus which appears by its size to be primarily suited for the processing of small quantities of plant material, it is to be understood that the present invention contemplates larger apparatus achieving a corresponding increase in processing capacity. Particularly in the instance where commercial processing is envisioned, the apparatus of the present invention may be modified to adapt to automated operation and may accordingly be associated with appropriate conveying and packaging machinery, so that plant material may be treated in bulk and thereafter immediately packaged for shipment, storage or end use.

Thus, for example, the heating apparatus may take the structure of a tunnel kiln or the like, not shown herein, wherein the plant material is placed in a hopper and immersed in an appropriate fluid medium, and thereafter subjected to the application of the heat at the predetermined temperature for a residence time within the kiln approximating the optimum heating cycle. The treated material then exits the kiln, remaining within the inert fluid medium, and may thereafter may conveyed to one of several stations for the aforenoted purposes.

Naturally, the foregoing description is illustrative of modifications which may be made in accordance with the present invention. The present invention is accordingly intended to embrace all such modifications within its spirit and scope. Thus, such additional operations as potency sensing by means of fluorescent inspection with a device such as a photo fluorometer may be employed in the instance where predetermined THC content is desirably imposed.

The method of the present invention can thus be seen to accomplish the rapid and efficient conversion of the plant material without the attending difficulties of destructive pyrolysis and degradative oxidation. Likewise, the apparatus of the present invention is of simple construction and use and is reliably consistent in its operation.

As noted earlier with respect to the inventive apparatus, a wide variety of materials may be employed in its construction. Thus, container 2, including base 4 and cover 6 may be prepared from materials such as glass, metal, plastic and the like, while heating means 18 is preferrably prepared from appropriate conductive metals and basket 10 is desirably prepared from a flexible material such as thermoplastic and thermosetting organic resinous materials. Though the accompanying drawings illustrate the construction of the respective components from particular materials, it is to be understood that the invention contemplates the employment of equivalent materials for each component, and is not limited to the selection of any particular material therefor.

It is to be understood that the invention is not limited to the illustrations described and shown herein, which are deemed to be merely illustrative of the best modes of carrying out the invention, and which are suitable of modification of form, size, arrangement of parts and details of operation. The invention rather is intended to encompass all such modifications which are within the spirit and scope and defined by the claims.

What is claimed is:

1. A method of treating a plant material consisting essentially of the plant cannabis, which contains a chemical ingredient comprising an organic carboxylic acid, which method comprises placing the plant material in a fluid medium which is essentially non-oxidizing to said plant material, and heating said plant material while in said fluid medium at a temperature of from about 95° C. to about 120° C. to cause the decarboxylation of said carboxylic acid, whereby said plant material contains the maximum possible amount of delta-9-tetrahydrocannabinol.

2. The method of claim 1 wherein said cannabis is selected from the group consisting of *Cannabis sativa, Cannabis indica* and *Cannabis ruderalis.*

3. The method of claim 1 wherein said organic carboxylic acid comprises cannabinolic acid.

4. The method of claim 1 wherein said fluid medium is selected from the group consisting of inert liquids, inert gases and mixtures thereof.

5. The method of claim 4 wherein said fluid medium comprises an inert liquid, and said inert liquid comprises water.

6. The method of claim 4 wherein said fluid medium comprises an inert gas, and said inert gas is characterized by the absence of releasable active oxygen.

7. The method of claim 6 wherein said plant material is placed within said fluid medium by confinement within an airtight container within a substantially non-oxidizing, inert gaseous atmosphere.

8. The method according to claim 1 wherein said heating is carried out for a period of up to about one hour.

9. The method of claim 1 wherein the plant material is cooled following said decarboxylation step.

10. The method in accordance with claims 1 or 9 wherein the decarboxylated plant material is maintained in an essentially non-oxidizing atmosphere after the completion of said heating step.

* * * * *